United States Patent [19]
Fischer et al.

[11] Patent Number: 5,890,900
[45] Date of Patent: Apr. 6, 1999

[54] DENTAL WEDGE WITH NON-SLIP HEAD

[75] Inventors: Dan E. Fischer, Sandy; Bruce S. McLean, West Jordan, both of Utah

[73] Assignee: Ultradent Products, Inc., South Jordan, Utah

[21] Appl. No.: 64,353

[22] Filed: Apr. 22, 1998

[51] Int. Cl.[6] .................................................. A61C 7/00
[52] U.S. Cl. ............................................................ 433/149
[58] Field of Search ............................................ 433/149

[56]  References Cited

U.S. PATENT DOCUMENTS

| | | | |
|---|---|---|---|
| 350,150 | 10/1886 | Parr | 433/149 |
| 2,150,005 | 3/1939 | McNinch | 433/149 |
| 3,193,094 | 7/1965 | Schulstad | 433/149 |
| 3,510,948 | 5/1970 | Walthall | 433/149 |
| 4,337,041 | 6/1982 | Harsany | 433/149 |

Primary Examiner—John J. Wilson
Attorney, Agent, or Firm—Workman, Nydegger, Seeley

[57]  ABSTRACT

An improved dental wedge has a body coupled to a head configured to prevent slipping of a dental instrument used to grip the wedge. The head has multiple flat gripping surfaces which enable a practioner to securely grasp the wedge from a variety of different angles. The head preferably has non-slip surfaces such as a resilient, compressible cap, a textured surface, or a coating. A neck preferably couples the head to the body. The neck is configured to be smaller in diameter than the body and the head. Because of the neck, the wedge includes a groove for placement of a dental instrument therein. The neck also preferably having a plurality of flat surfaces extending about a circumference thereof, the flat surfaces on the neck being preferably offset with respect to the flat surfaces on the head.

19 Claims, 12 Drawing Sheets

DENTAL WEDGE WITH NON-SLIP HEAD

BACKGROUND

1. Field of the Invention

The invention disclosed herein are in the field of dental instruments. More particularly, the inventions relates to dental wedges which are utilized to separate teeth in preparation for a dental procedure and to instruments configured for use with dental wedges and to instruments utilized with the dental wedges.

2. Background Art

In the field of dentistry, dental practitioners often treat patients who have developed cavities on the side of a tooth. When these cavities are located adjacent to neighboring teeth they are known as interproximal cavities. In order to treat cavities on the sides of teeth such as interproximal cavities, the dental practitioner removes the infected portion of the tooth, then deposits a filling such as a resinous material or an amalgam into the tooth preparation.

In order to properly deposit the filling without undesired seepage of the filling material beyond the side of the tooth, typically a matrix band is disposed about the tooth, after which the filling material is deposited. A matrix band is typically a metallic or plastic strip having first and second ends which are joined, thereby forming a mold which is disposed about the tooth. When encircled about the tooth, the matrix band acts as a form, similar in function to a concrete form, providing a mold for the desired shape of the repaired tooth.

In order to maintain the matrix band in a desired position with respect to the tooth to be repaired, small dental wedges are placed in the interproximal spaces between the matrix band and the teeth adjacent the tooth to be repaired. The wedges also space the teeth adjacent to the tooth to be repaired during the filling procedure. Dental wedges may be used to spread adjacent teeth for a variety of purposes.

Because they are placed between the matrix band and adjacent teeth, dental wedges are required to be small. Their small size and the delicate nature of orienting the wedges correctly within the desired interproximal space in the mouth makes the placement of the wedges awkward.

Typical dental wedges include a distal insertion end and a proximal gripping end. Typical wedges also have a triangular cross section. This triangular cross section includes a thin apex at one end thereof and widens into a flat base at an opposing end thereof. In order to fit properly in an interproximal space, each wedge is typically placed with the widened end located toward the gum line and with the thin apex extending between the teeth and away from the gums. When using such dental wedges, the pracioner is careful to orient the wider end toward the gumline while the more thinner, pointed apex is directed upward between the teeth.

In light of this triangular configuration of typical wedges, it is important to orient the wedge properly with respect to the interproximal space before pressing the wedge into the interproximal space. In addition, the properly oriented wedge must be precisely guided into the space. Conventional wedges, however, are difficult to control such that the practioner can be assured that the wedge is properly oriented without making the patient uncomfortable or possibly damaging the gums and/or teeth of the patient.

In order to strategically align and guide the wedge properly, the practitioner is required to maintain a solid grip on the wedge. If the practitioner does not maintain a solid grip, the practitioner may drop the wedge before entering the oral cavity causing contamination, orient the wedge improperly, or even drop the wedge intraorally thus presenting the possibility of the wedge being swallowed or causing aspiration to the lung. However, the small wedges are difficult to grasp and maneuver with precision in the mouth with an unaided hand. Thus, a practitioner typically uses small-nosed pliers, known as cotton pliers, to grip a particular wedge and to position the wedge within the mouth.

Typical dental wedges are comprised of a rigid plastic or wood having a smooth exterior surface which compounds the difficulties associated with firmly gripping the wedges due to their small size. The smooth, rigid material readily slips from the pliers when tightly gripped, particularly when covered with fluids, such as saliva or blood.

The slippery nature of the wedge can cause the wedge to be lost within the patients' mouth or ejected from the pliers across the room. Even if the small wedge is found, often it cannot be utilized due to the likelihood of contamination. After the wedge is initially positioned, the dentist forces the wedge into final position. During the forced insertion, the likelihood of injury is greatest as the pliers or tweezers may slip off the wedge into the soft tissues in a patient's mouth. Additionally, when the dentist attempts to regrasp the wedge with cotton pliers there is also risk of slipping off the wedge.

FIG. 1 demonstrates a dental wedge 10 of the prior art. Because of the shape and also the rigid surface of the body 12 of wedge 10, pliers readily slip when contacting wedge 10. As shown in FIG. 2, in certain wedges 14 of the prior art, a head 16 is disposed on the proximal end of the body 18 of wedge 14. However, head 16 and body 18 are both typically comprised of a rigid material which slips when grasped by or pushed by a dental instrument. Thus, grasping either head 16 or body 18 often causes wedge 14 to be ejected from the pliers.

Furthermore, head 16 is square in shape, having only four gripping surfaces along the circumference of head 16. Therefore, to grasp head 16 on the circumference thereof, the pliers must be oriented along one of two gripping angles. In the first gripping angle, the practitioner grips sides 20 of head 16. In the second angle, the practitioner grips the upper end 22 and lower end 24 of head 16. However, when reaching through the fixed diameter of the mouth, the practitioner may not have the option of twisting the pliers to mate with a four sided head along one of only two gripping angles.

As shown in the embodiment of FIG. 3, head 26 of another dental wedge 28 is curved, thereby creating a slippery dynamic when the practitioner attempts to grasp dental wedge 28 by head 26. Because of the delicate nature of typical dental procedures, this slippery action of prior art wedges creates a variety of problems for the dental practitioner.

There is, therefore, a need in the art for a dental wedge which is readily grasped by a practitioner from a variety of positions and angles.

BRIEF SUMMARY AND OBJECTS OF THE INVENTION

It is therefore an object of the invention to provide an improved dental wedge.

It is another object of the invention to provide a dental wedge which is easily grasped by a dental instrument, such as tweezers or cotton pliers.

It is also an object of the invention to provide means for preventing slipping of a dental tool used to grip the wedge.

Additionally, it is another object of the invention to provide a dental wedge having a non-slip neck which can be more easily positioned than conventional wedges from multiple positions and angles.

Finally, it is another object to provide dental instruments which are adapted for grasping a dental wedge.

One invention relates to a dental wedge, comprising: (i) a body having a proximal end and a distal end; and (ii) a head coupled to the body. The head of the wedge has more than four different flat sides extending about the circumference of the head which serves as gripping or bracing surfaces. The head preferably has six, eight or more different flat gripping surfaces. The head has a polygonal shape such as a hexagonal, octagonal, or decagonal shape. Because of the number of flat gripping surfaces, an increased number of angles and positions exist from which the practitioner can grasp the dental wedge. A practitioner is thus more likely to achieve a grip which will sufficiently hold the wedge.

Additionally, the head preferably has a cap located in the proximal end of the head. The cap is formed from an elastomeric material which compresses when a dental instrument is urged against the cap to push the wedge into position between two teeth. The elastomeric cap essentially grips the dental instrument to prevent the dental instrument from slipping or sliding off of the cap. In addition to an elastomeric cap, the head may also be designed to have other non-slip surfaces such as textured surfaces or surfaces coated with a tacky material. The textured surface may an integral portion of the proximal end of the head or a cap may be utilized which is textured. Similarly, a tacky coating may be applied onto the proximal end of a head or onto a cap. Additionally, the proximal end of a head or the cap may also have a particular structure, such as a concave or dimpled configuration, which is designed to minimize slipping. These non-slip surfaces may be utilized alone or in combination to prevent a dental instrument from sliding.

In another embodiment, a neck couples the head to the body. The neck has a smaller diameter than the adjacent portion of the head or body. As a result of the decreased diameter neck, the wedge includes a groove in which the tweezers or pliers may be disposed, allowing the practitioner to more readily grip the wedge. Accordingly, the practitioner can optionally firmly grasp the neck, push within the groove against the body to place a wedge in a patient's mouth or pull against the head to remove the wedge while a dental instrument remains stable and is securely within the groove.

In addition, the neck preferably includes a plurality of different flat gripping surfaces extending about the circumference of the neck for disposition of the tweezers or pliers thereon. The flat gripping surfaces of the neck provide additional positions from which a practitioner is able to grasp the wedge. To dramatically increase the number of positions from which a practitioner is able to grasp the wedge, the flat gripping surfaces of the head may be offset with respect to the flat gripping surfaces of the neck.

By way of example, if the head includes the shape of an octagon, the practitioner is able to grip the circumference of the head from at least four different angles. The practitioner is able to grip the circumference of the neck from at least four different angles at another location if the neck also includes the shape of an octagon. If the surfaces on the neck are offset with respect to the surfaces on the head, the practitioner is able to grip the circumference of the head and neck region of the wedge from at least eight different angles.

Another invention relates to dental instruments which are adapted for grasping a dental wedge. Each instrument has surfaces which are configured to be mated with the flat gripping surfaces of the head or neck of wedge of the present invention. One embodiment is a pair of tweezers with flat grasping surfaces formed in the internal side of each arm or elongated member. The tweezers can securely grasp the neck or head of a wedge. Another embodiment of a dental instrument adapted for grasping a dental wedge is a wrench having a grasping end. The grasping end of the wrench may be open such that the end may grasp the head or neck of the wedge to remove the wedge from an embrasure or to pull the wedge out of an embrasure. The grasping end of the wrench may also be closed such that it forms a socket which fits over the head of a wedge to push the push the wedge into position.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are therefore not to be considered limiting of its scope, the invention will be described with additional specificity and detail through the use of the accompanying drawings in which.

DETAILED DESCRIPTION OF THE PREFERRED EMBODIMENTS

The wedge of the present invention is useful for maintaining a matrix band in a desired orientation, creating a space between teeth or providing other dental or non-dental functions. The wedges have various gripping and non-slip surfaces which enable a practitioner to achieve a suitable grip, retain the wedge in a desired, fixed position with respect to a dental instrument, and safely position the dental wedge between teeth. The gripping and non-slip surfaces also enable a practitioner to remove the wedge upon completion of a dental procedure by grasping the wedge with a dental instrument and then pulling without the dental instrument slipping off wedge.

Figure 4:
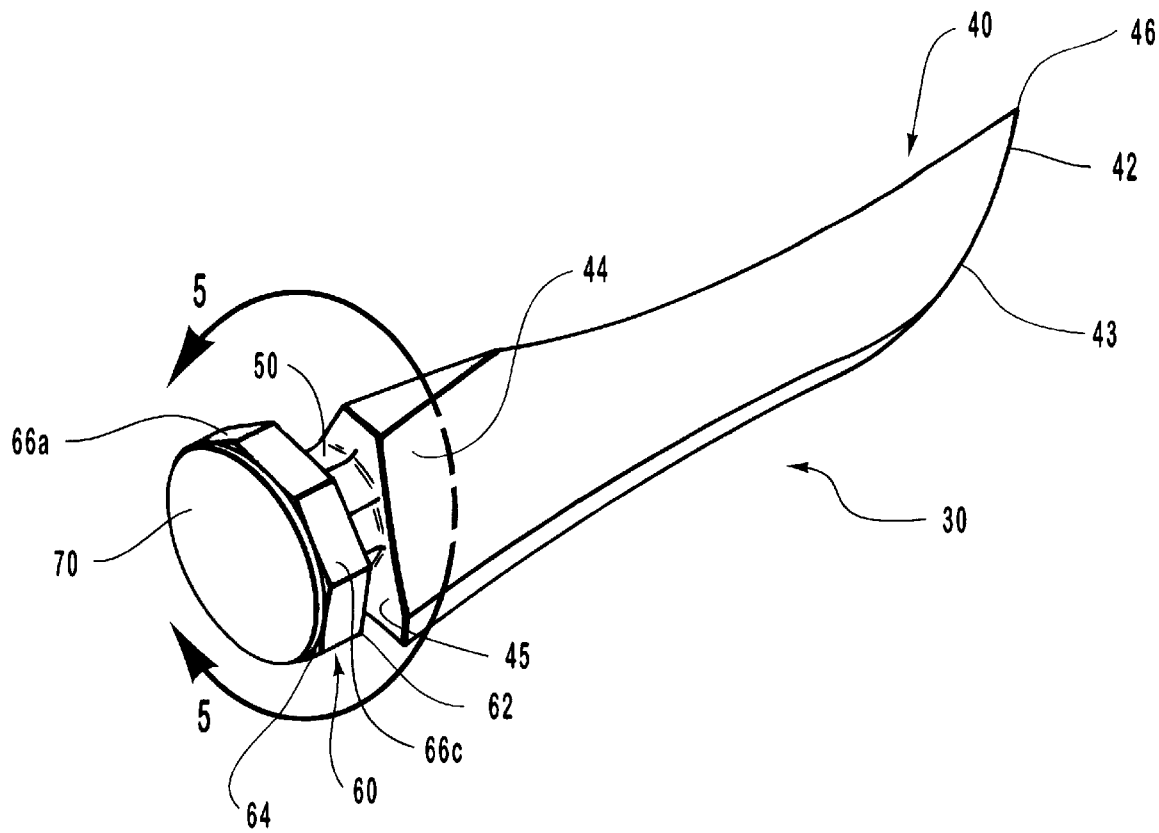
FIG. 4 is a perspective view of a dental wedge of the present invention.
Figure 5:
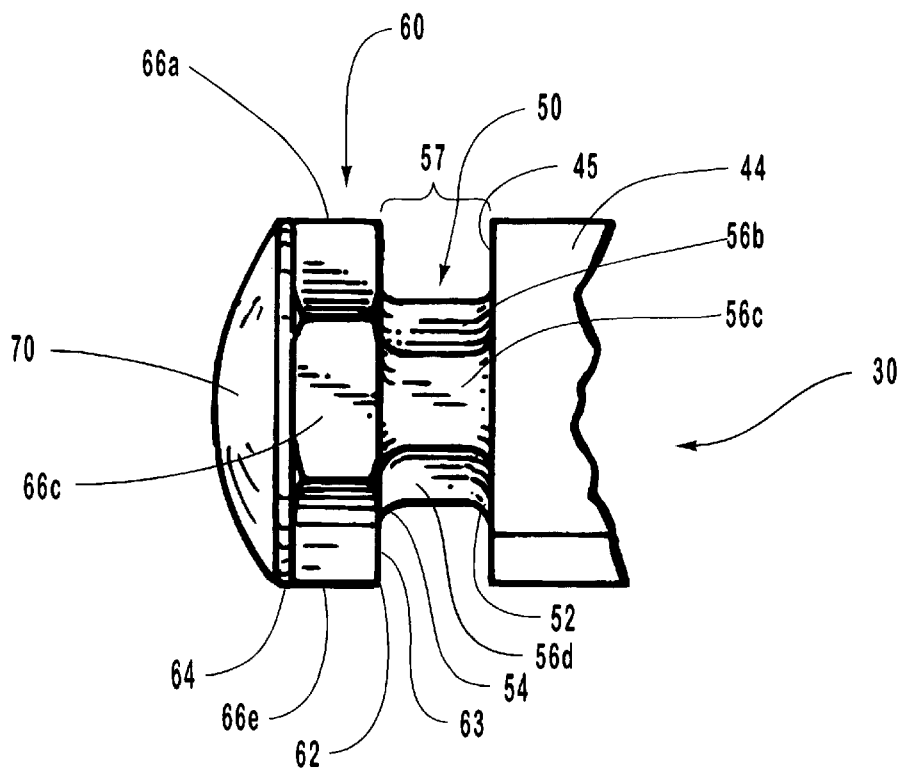
FIG. 5 is an enlarged side view of the head and neck of the wedge shown in FIG. 4.
Figure 6:
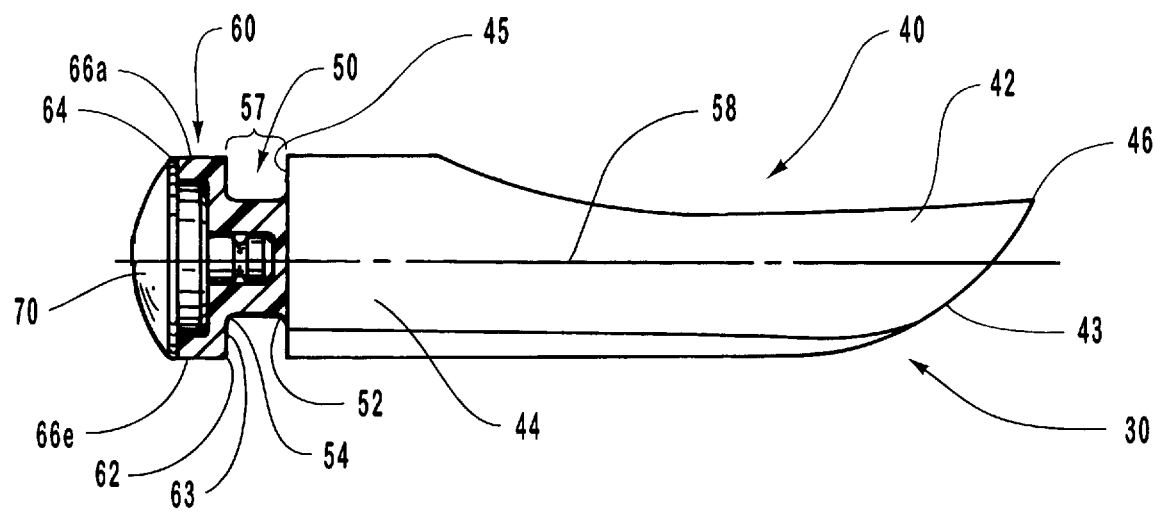
FIG. 6 is a side view of the neck and head of the dental wedge of FIG. 4 with a partial cut-away cross-sectional view of the neck and head.

As shown in FIGS. 4–6, a dental wedge 30 of the present invention is comprised of (i) a body 40 having a distal insertion end 42 and a proximal end 44; and (ii) a head 60 coupled to body 40, head 60 having a distal end 62 and a proximal end 64. Also as shown, a neck 50 preferably couples head 60 to body 40. Other embodiments of dental wedges of the present invention are also shown in FIGS. 13–18.

As shown, distal end 52 of neck 50 is coupled to proximal end 44 of body 40. The proximal end 54 of neck 50 is coupled to distal end 62 of head 60. Wedge 30 has a longitudinal axis demonstrated by line 58 shown in FIG. 6.

Figure 9:
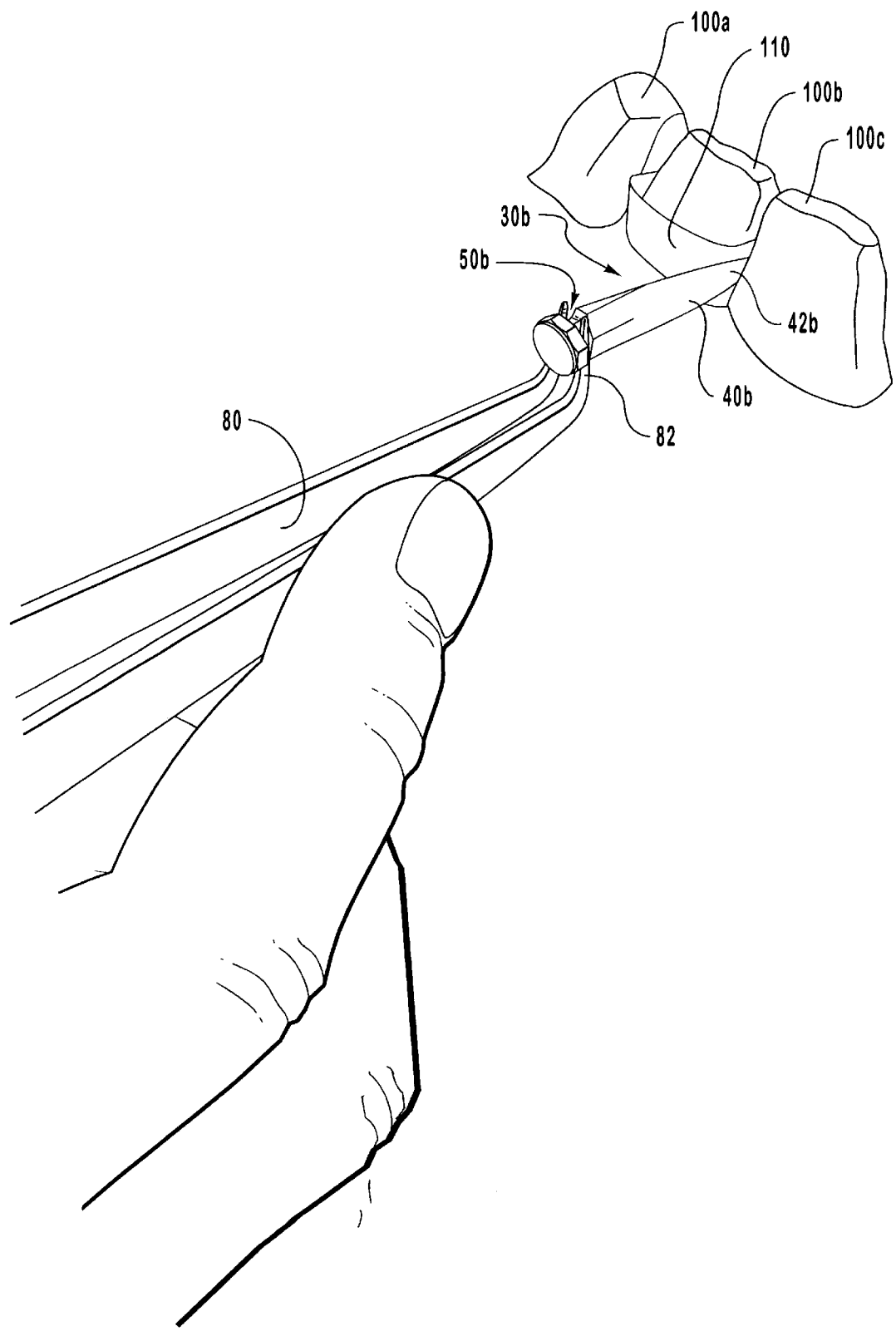
FIG. 9 is a perspective view of a user's hand grasping a dental wedge by the neck of the dental wedge with cotton tweezers and inserting the distal insertion end of the dental wedge into an embrasure or interproximal space adjacent a matrix band disposed about a tooth.
Figure 10:
FIG. 10 is a perspective view of a user's hand pushing on the head of a dental wedge with the blunt end of cotton tweezers to further insert the dental wedge between the teeth.
Figure 11:
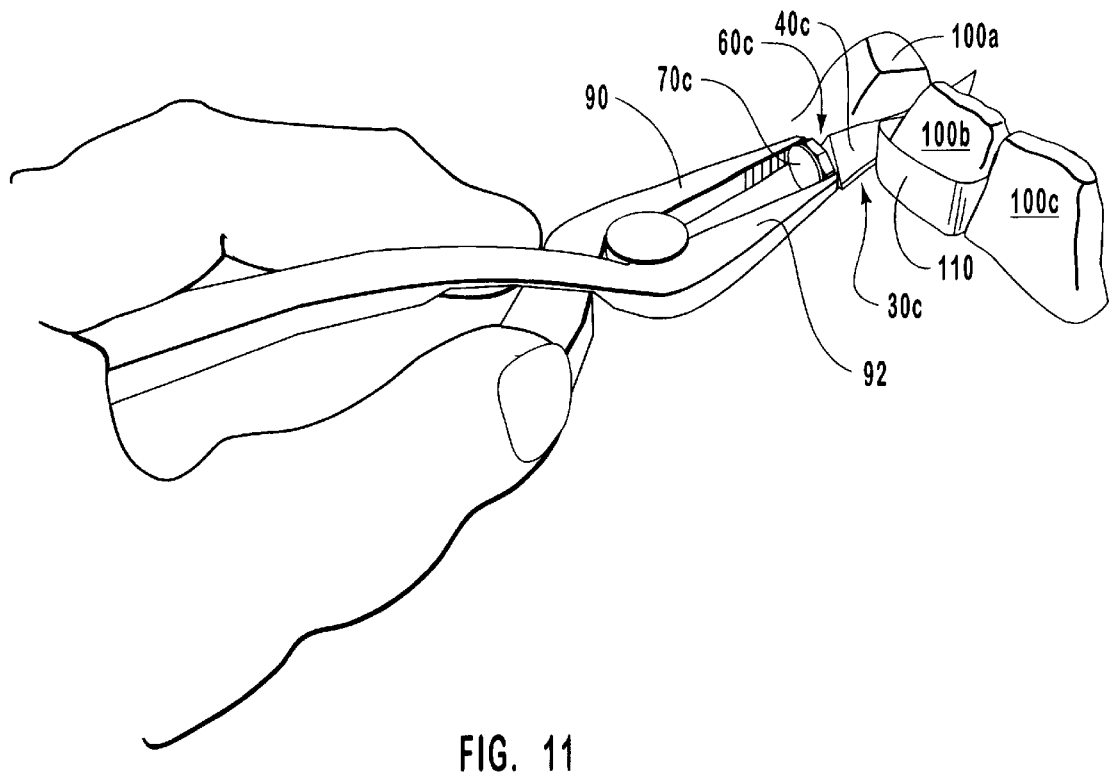
FIG. 11 is a perspective view of a user's hand pulling on the head of a dental wedge with pliers to remove the dental wedge from between the teeth.

The body of the wedge may have any configuration suitable for insertion into an embrasure or within an interproximal space between two teeth. As shown in FIG. 4, the preferred configuration of the body of the wedge generally has a relatively thin distal insertion end with a bottom portion 43 that is relatively curved and which terminates at a pointed tip 46. The body preferably flares from the distal insertion end toward the proximal end 44 such that the body has a triangular cross-section of increasing size. The thin distal portion permits the practitioner to initially dispose wedge 30 between the patients'teeth. The taper of body 40 enables a practitioner to move teeth relative to each other as pressure is exerted on the wedge. More specifically, as the wedge is pushed inward, the cross section of the wedge between the teeth becomes increasingly wider, thereby enabling relative teeth movement. At least one corner at the proximal end is preferably truncated to provide increased leverage in separating or displacing teeth. As previously discussed, separation of the teeth enables a practitioner to position a matrix band around a tooth. The sides of the matrix band are then joined by an elastic band, such that the band forms a sleeve or a form about the tooth as shown in FIGS. 9–11 at 110. Disposing wedge 30 between the patient's teeth against matrix band 110 also helps to ensure that matrix band 110 is held against the prepared tooth.

Figure 8:
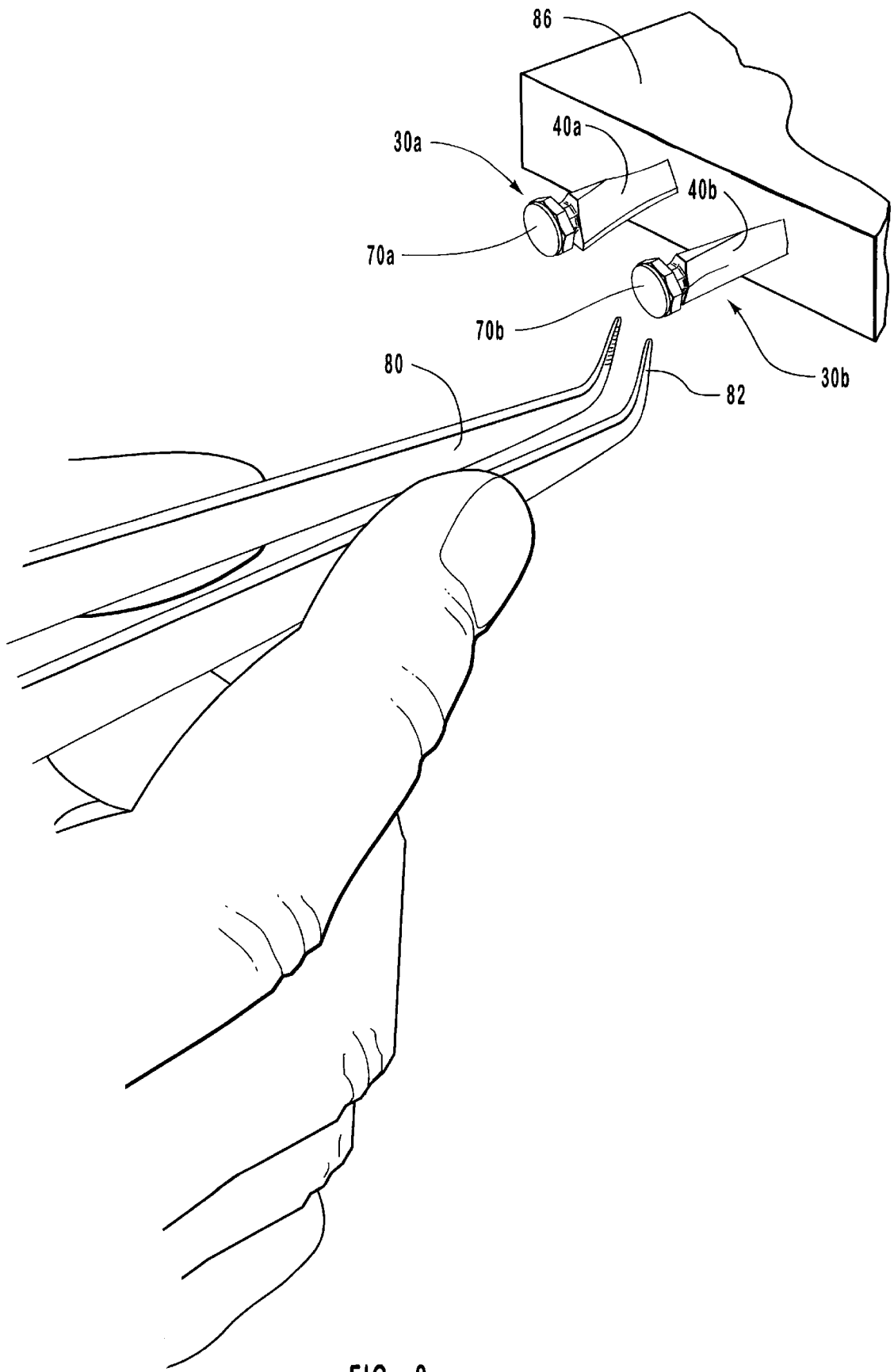
FIG. 8 is a perspective view of a user selecting a dental wedge from a set of dental wedges with different flares.

As shown in FIG. 8, a kit may be provided of at least two wedges and the wedges may have differing configurations. More particularly, the bodies of the wedge may have different flares or tapers as depicted in FIG. 8 at 40*a* and 40*b*. Bodies 40*a* and 40*b* of wedges 30*a* and 30*b* each have a triangular cross section, however, body 40*a* has a wider base and apical angle than does body 40*b*. In addition to the width of the base, the pitch or apical angle, the bodies of the wedges may also have differing heights. FIG. 8 also shows wedges 30*a* and 30*b* standing upright in a support material 86 which is preferable for maintaining the wedges in a sterile or nearly sterile condition.

The various embodiments of wedge bodies disclosed herein, including the prior art body configurations discussed hereinabove, are examples of tapered body means for insertion within an interproximal space between two teeth. Additionally, any conventional body configuration may also be utilized.

As shown in FIG. 8 and FIG. 9, a user can easily grasp a wedge with the prongs 82 or grasping end of conventional cotton pliers 80. FIG. 9 shows prongs 82 grasping wedge 30*b* by neck 50*b* as distal insertion end 42*b* is being pushed into an interproximal space. The base or widened end of the wedge is located toward the gum line and the thin apex extends between the teeth 100 and away from the gums. The body can be initially inserted or pushed completely into position by grasping the neck and/or by pushing against the face of the proximal end of the body, such as face 45 shown in FIG. 4 and FIG. 5 at 45. One preferred technique for pushing the body of a wedge completely into position is depicted in FIG. 10 wherein the blunt end 84 of conventional cotton pliers 80 is shown being utilized to push body 40*a* of wedge 30*a* further between the teeth. A wedge can be easily removed by pulling while grasping the neck as shown in FIG. 9 with prongs 82 of tweezers 80 and/or by pulling against the face of proximal end of the head, such face 63 shown in FIG. 5 at 63. Additionally, a wedge may be removed from an embrasure by grasping the head with conventional cotton tweezers or as is shown in FIG. 11 the head 60*c* of a wedge 30*c* may be grasped and pulled with the grasping end 92 of pliers 90. While the instruments disclosed in FIGS. 9–11 for inserting and removing the dental wedges are acceptable, inventive instruments which are particularly adapted for use with the inventive dental wedges are also disclosed herein.

As best shown in FIGS. 4–5, neck 50 has a smaller diameter than distal end 62 of head 60 and proximal end 44 of body 40, thereby forming a groove 57 for placement of a dental instrument therein. Groove 57 is defined by (i) proximal end 44 of body 40; (ii) the exterior surface of neck 50; and (iii) distal end 62 of head 60. Essentially, the reduced diameter neck 50 is any depression or groove located between the head and the proximal end of the face.

Figure 12:
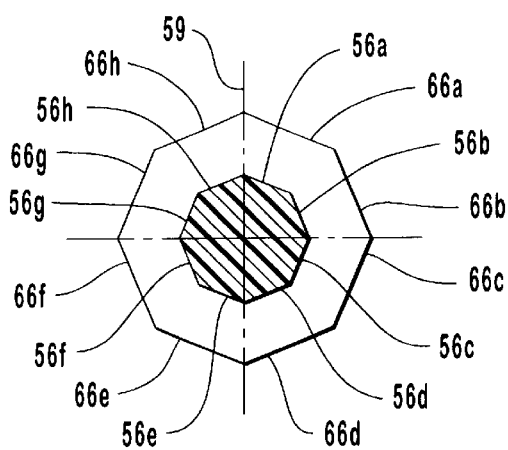
FIG. 12 is a cross sectional view of a head and neck of the dental wedge of FIG. 4 and FIG. 5, the flat surfaces of the head being aligned along an axis with the flat surfaces of the neck.

FIGS. 4–5 and FIG. 12 also depict neck 50 having eight different flat gripping surfaces 56a–h extending about the circumference of the surface of the neck, such that a transverse cross section of neck 50 has the shape of an octagon. The neck preferably has eight different flat gripping surfaces as shown at 56a–h, however, the neck may have any suitable configuration. For example, the neck may have a cross-section which is generally circular, elliptical, triangular, or the neck may have four or more different flat gripping surfaces extending about the circumference of the surface of the neck such that the cross-section is that of a square, a pentagon, a hexagon, a decagon and so on. Even numbers of flat surfaces are preferred for the neck, but not required. Nevertheless, neck 50 preferably includes the shape of a polygon having more than four sides. As a result of the multiple surfaces on neck 50, neck 50 may be grasped from a variety of different gripping angles and positions. Additionally, the circumference of neck 50 is preferably symmetrical.

Each neck disclosed herein is an example of neck means for receiving a grasping end of a dental instrument to move the tapered body means with respect to an interproximal space between two teeth, and for coupling the distal end of the head means to the proximal end of the tapered body means. In alternative embodiments, the surface of the neck may be textured or coated with a tacky material. Additionally, a flexible and compressible washer may be positioned around the neck. Such texturing, coatings and washers are examples of means for preventing slipping of a dental instrument urged against the wedge, or more specifically a dental instrument used to grasp the wedge or neck.

Like neck 50, head 60 is also shown in FIGS. 4–5 and in FIG. 12 with eight different flat sides at 66a–h. The head may have any suitable configuration, however, the head preferably is in the shape of a polygon with more than four different flat sides extending about the circumference of the head. Examples of such shapes include a pentagon, hexagon, octagon, a decagon and so on. Thus, the cross section of head 60 transverse to axis 58 may be in the shape of a pentagon, hexagon, octagon, decagon and so on. As shown, the circumference of head 60 is preferably symmetrical since each flat side has the same dimensions. While not required, the number of different flat gripping surfaces 66 of head 60 is preferably even, such as six, eight, ten, and so on as it is for flat gripping surfaces 56 disposed about the circumference of neck 50.

Figure 1:
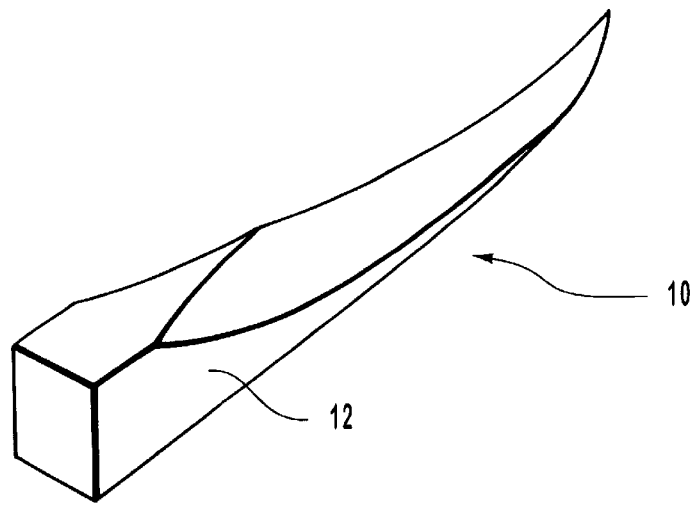
FIG. 1 is a view of a dental wedge of the prior art.
Figure 2:
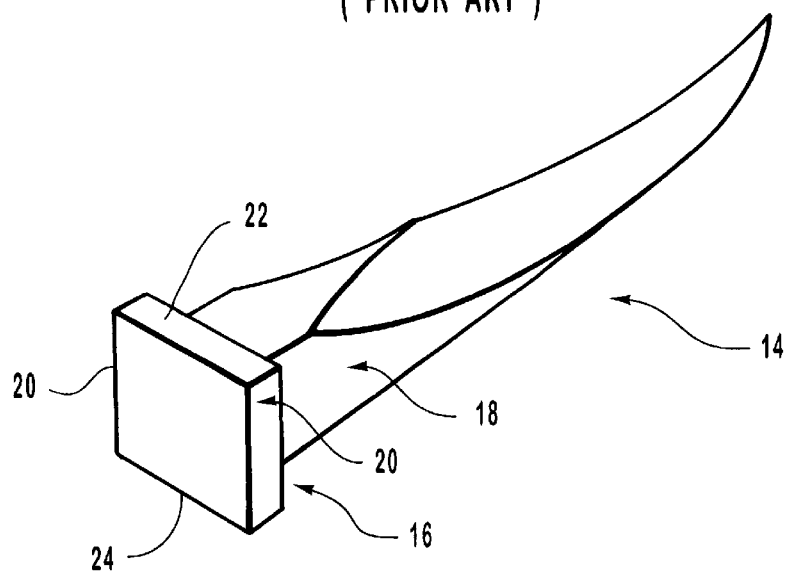
FIG. 2 is a view of another dental wedge of the prior art.
Figure 3:
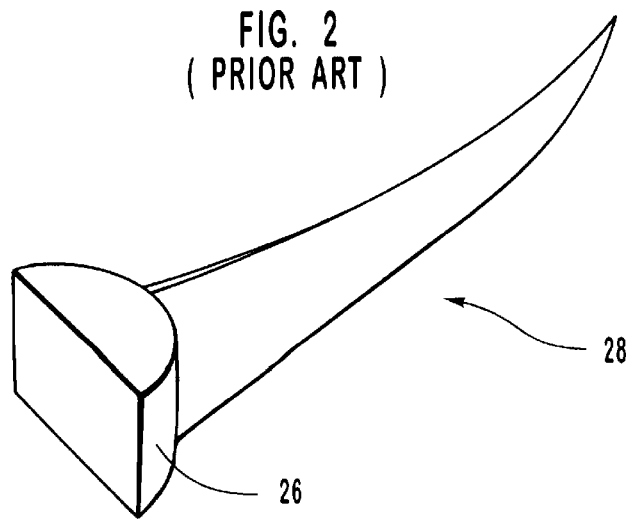
FIG. 3 is a view of yet another dental wedge of the prior art.

Thus, rather than having limited gripping angles, as is the case with a square shaped head 16 of FIG. 2, head 60 has many different gripping angles. Since some gripping angles may not be accessible due to the location of the embrasure into which the wedge is being positioned, it is preferable to have a high number of choices for the gripping angle. Accordingly, the transverse cross section is preferably that of a hexagon, an octagon, a decagon, and so on to provide a large number of different gripping angles.

Figure 7:
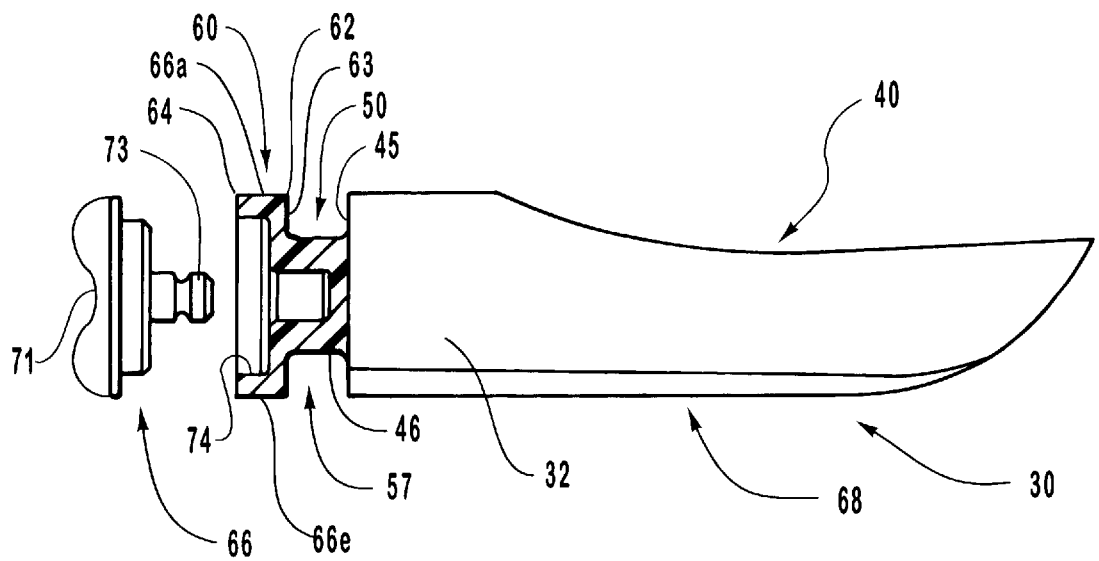
FIG. 7 is an exploded view of the embodiment shown in FIGS. 4–6 which depicts the cap detached from the proximal end of the head of the dental wedge. The dimpled cap depicted in FIG. 7 is a different embodiment of a cap.

It will be appreciated that each gripping angle corresponds to a number of different gripping positions. For example, if a practitioner grips the top and bottom surfaces 66a and 66e of head 60, as shown in FIG. 5 and FIG. 7, which is an example of one gripping angle, the practitioner's hand may be oriented in a variety of different positions while holding tweezers or pliers. In the octagonal embodiment, for example, a practitioner's pliers can grip the top and bottom surfaces 66a and 66e or any other combination of opposing surfaces. As a result, when reaching from an awkward position into the mouth, a practitioner is more likely to achieve a suitable grip, to retain wedge 30 in a desired, fixed position in a dental instrument, and to sufficiently position dental wedge 30 between teeth.

FIG. 12 is a cross sectional view of head 60 and neck 50 of wedge 30 shown in FIG. 5. In the embodiment shown in FIG. 12, the flat surfaces 66a–h extending about the circumference of head 60 and the flat surfaces 56a–h extending about the circumference of neck 50 are aligned with each other along an axis 59. Accordingly, any two opposing sides such as 66b and 66f or 56c and 56g may be easily grasped.

Figure 13:
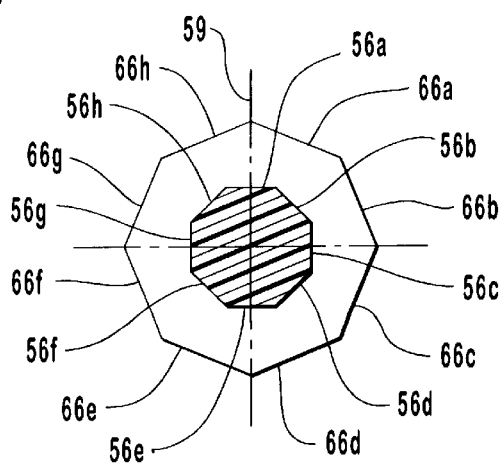
FIG. 13 is an alternative cross sectional view of the head and neck of a dental wedge, the flat surfaces of the neck being offset from the flat surfaces of the head.

In another embodiment of a dental wedge shown in FIG. 13, the head and the neck each have a plurality of flat surfaces respectively identified at 66a–h and 56a–h. Flat surfaces 66a–h of the head and the flat surfaces 56a–h of the neck are offset with respect to flat surfaces each other such that 66a is not parallel with 56a as in the configuration shown in FIG. 12.

By offsetting the respective gripping surfaces 66a–h and 56a–h respectively of the head and neck as shown in FIG. 13, it is possible to create even more gripping angles than are available individually on the embodiment shown in FIG. 12. The increased number of gripping angles and positions created by the offset nature of the head and neck is a significant advance within the art. Although, the embodiment shown in FIG. 13 offers greater gripping angles which makes it easier to push or pull the wedge, the embodiment shown in FIG. 12 is easier to mold.

When reaching through the fixed diameter of the mouth to typical wedges, a practitioner may not have the option of twisting the tweezers or pliers along one of two angles to grasp a four-sided head, such as head 16 shown in FIG. 2. If more than two gripping angles are available, however, such as shown in FIGS. 12 and 13, a practitioner's chances are vastly improved of securely grasping a wedge as needed. It will be appreciated that in addition to grasping head 60 and/or neck 50, the practitioner may also grip body 40 as well.

Because of the various surfaces of the wedge, the practitioner has the option of grasping and pulling, grasping and pushing, or pushing against a variety of different structures on the wedge 30. Additionally, the head and neck may be grasped from a variety of different positions around the circumference thereof. In a preferred method of using the wedge, prongs or grasping end 82 of tweezers 80 are used to grasp neck 50 and initially position the wedge into an embrasure as shown in FIG. 9. More specifically, prongs 82 are pushed against proximal end 44 of body 40 or are used to firmly grasp neck 50 while pushing against proximal end 44 to push wedge 30 into a desired location. The body of the wedge is then fully inserted into position as shown in FIG. 10 by urging the blunt end 84 of tweezers 80 against head 60. Removal is preferably accomplished in the same manner shown in FIG. 9 for initial placement by gripping neck 50 and then pulling the wedge out of the embrasure. More specifically, wedge 30 may be pulled from the embrasure by pulling against the distal end 62 of head 60 with prongs 82, by firmly grasping neck 50 and pulling, or by grasping neck 50 while pulling against distal end 62.

Figure 14:
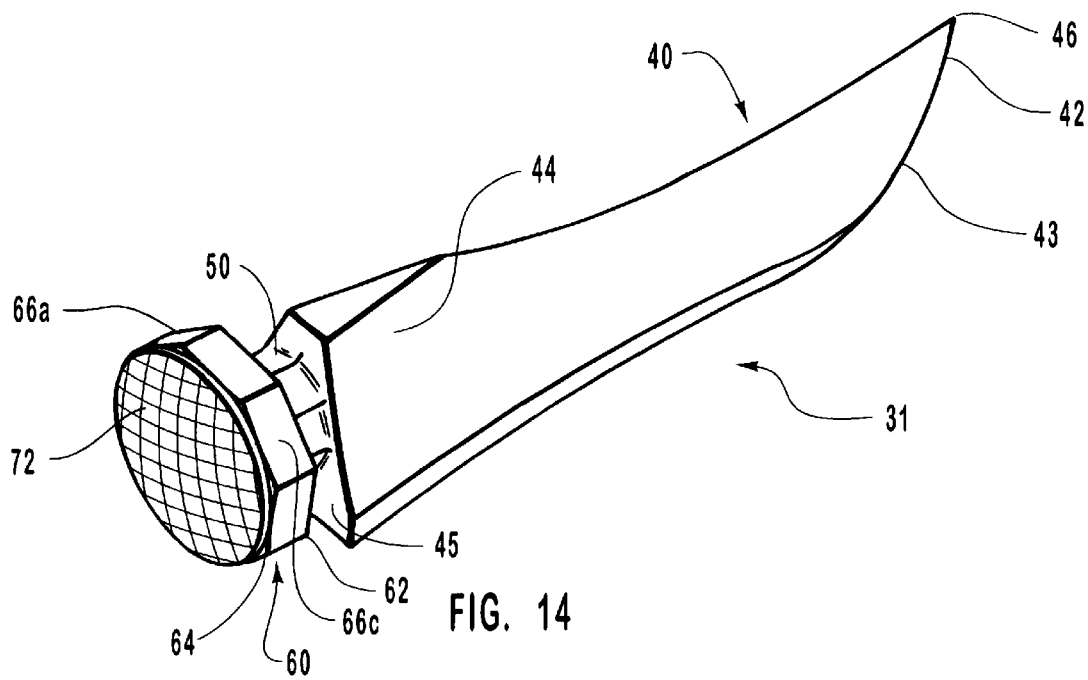
FIG. 14 is a perspective view of another embodiment of a dental wedge of the present invention which has a head with a textured cap or proximal end.

FIGS. 4–6 and 8–11 depict proximal end 42 as having a cap 70. Other embodiments of caps are shown in FIG. 7 and FIG. 14 respectively at 71 and 72. As shown most clearly in FIG. 7, each cap preferably has an insertion prong 73 which fits into a chamber 74 extending through head 60 and neck 50. Insertion prong 73 is an example of an attachment means for attaching a cap to a head which is adapted to receive a cap. Another example of an attachment means is adhesive. The adhesive may be applied between the cap and a head with a shape that is adapted to be mated with the opposing surface of the cap. Such mated surfaces include flat surfaces.

Caps 70, 71 and 72 are preferably comprised of a material, such as an elastomer, which is resilient and which compresses when pushed or gripped. Although any suitable material may be used, caps 70, 71 or 72 are preferably formed from elastomers such as neoprene, silicone, polyurethane, polypropylene, latex, rubber, etc.

When pushed with the blunt end 84 of tweezers as shown in FIG. 10, cap 70 compresses, avoiding a slippery dynamic which may result with a rigid surface. Rather than sliding on a rigid surface, blunt end 84 of tweezers 80 indents into the resilient, compressible material. As best viewed in FIG. 6, cap 70 has a convex surface as more compressible material is disposed in the center of the convex surface than on the periphery. By enabling the cap to indent, the surface area contacted by the instrument is increased thereby decreasing the potential for slipping.

While cap 70 is essentially convex, cap 71 is essentially concave or dimpled. By positioning a dental instrument at or near the low point in dimpled cap 71, the concavity assists in preventing a dental instrument from slipping off of cap 71. The concavity can be relatively shallow or relatively deep.

The textured surface of cap 72 shown in FIG. 14 of wedge 31 provides even greater resistance against slipping as a user pushes an instrument against the cap than does a compressible cap with a smooth surface such as cap 70. The textured surface of cap 72 is formed to have raised surfaces or is roughened to prevent dental instruments from sliding across the surface. The textured surface could be, for example, comprised of knurls, cuts, grooves, or other texturing such as chemical etching or gritblasting. Textured surfaces may be utilized on any cap configuration. For example, a concave cap such as cap 71 may be configured with a textured surface such as cap 72.

Each cap disclosed herein is an example of a non-slip surface or means for preventing slipping of a dental instrument urged against the wedge, or more particularly to prevent slipping of a dental instrument when pushing against head 60. Another example of a non-slip surface or means for preventing slipping of a dental instrument is a cap such as cap 70, 71 or 72 which has been coated with a relatively tacky material.

Figure 15:
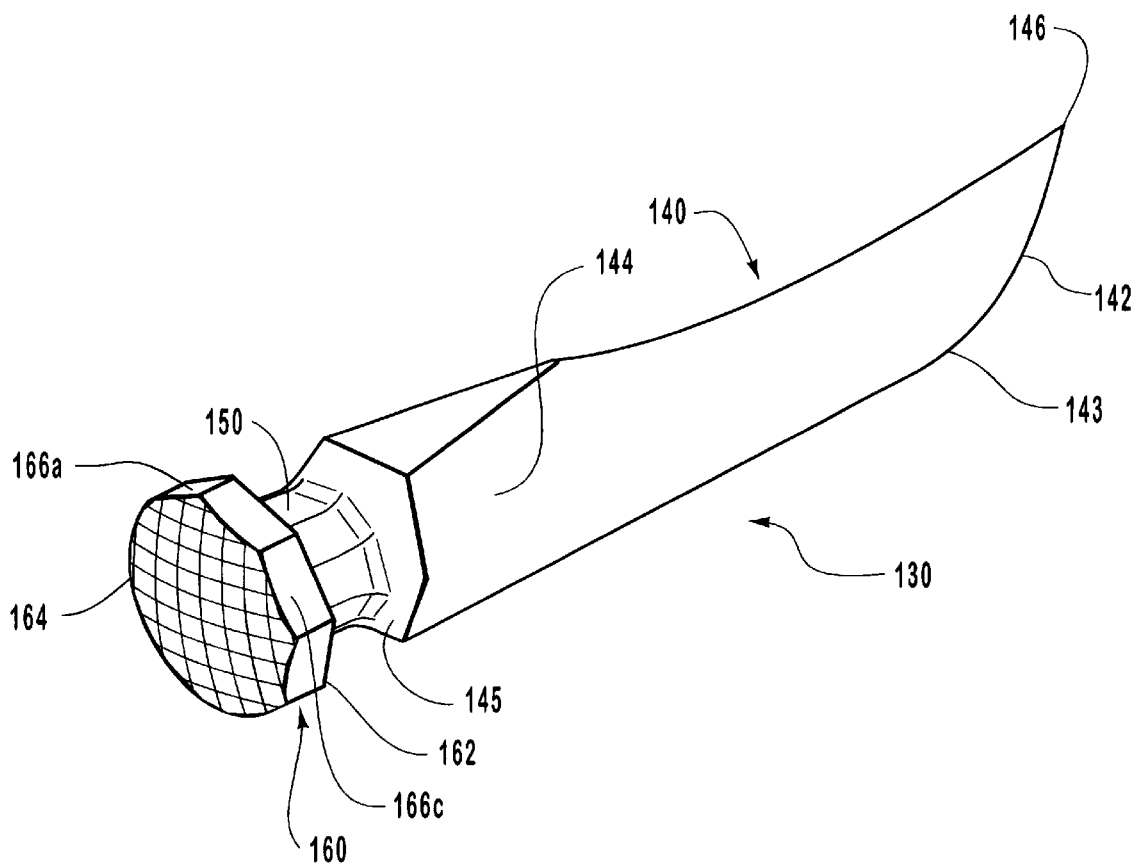
FIG. 15 is a perspective view of another embodiment of a dental wedge of the present invention which has an integral head with a textured proximal end.

FIG. 15 depicts a wedge at 130 with a head 160 having a proximal end 164 which is textured. The textured surface of proximal end 164 is another example of means for preventing slipping of a dental instrument. The compressible caps 70, 71 and 72 used with wedge 30 provide greater resistance to slipping, however, wedge 130 can be more easily manufactured as it is entirely one component.

Figure 16:
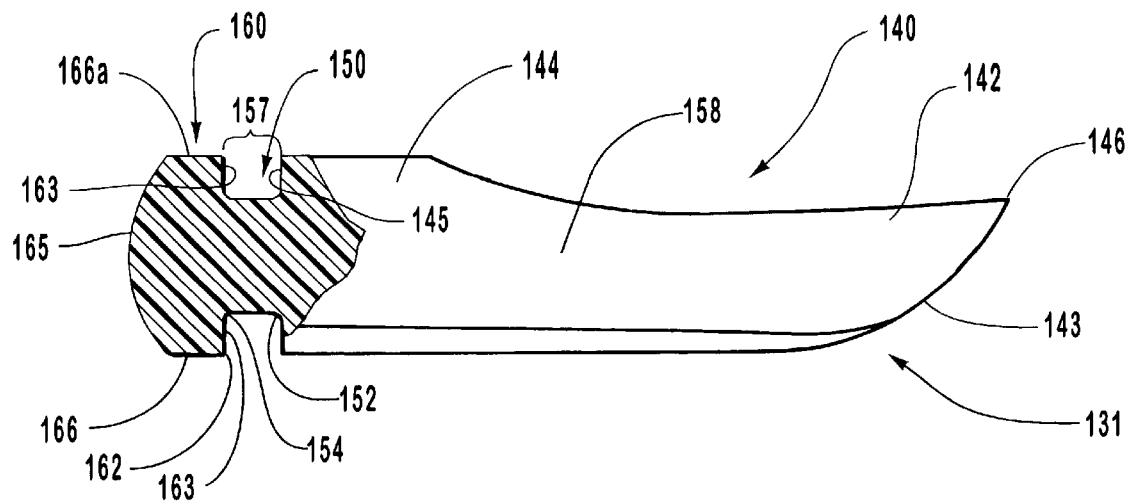
FIG. 16 is a perspective view of another embodiment of a dental wedge of the present invention which has a head with a textured proximal end.

FIG. 16 depicts another embodiment of a dental wedge of the present invention at 131. Head 160 of wedge 131 has a proximal end 165 which is smooth and does not have a cap. Like wedge 130, wedge 131 is also entirely integral and accordingly less expensive to manufacture than wedges 30 or 31. Proximal end 165 of wedge 131 and also proximal end 164 of wedge 130 may be coated with a relatively tacky material to provide increased resistance to slipping. A coating on either proximal end 164 or 165 provides another example of means for preventing slipping of a dental instrument.

Figure 17:
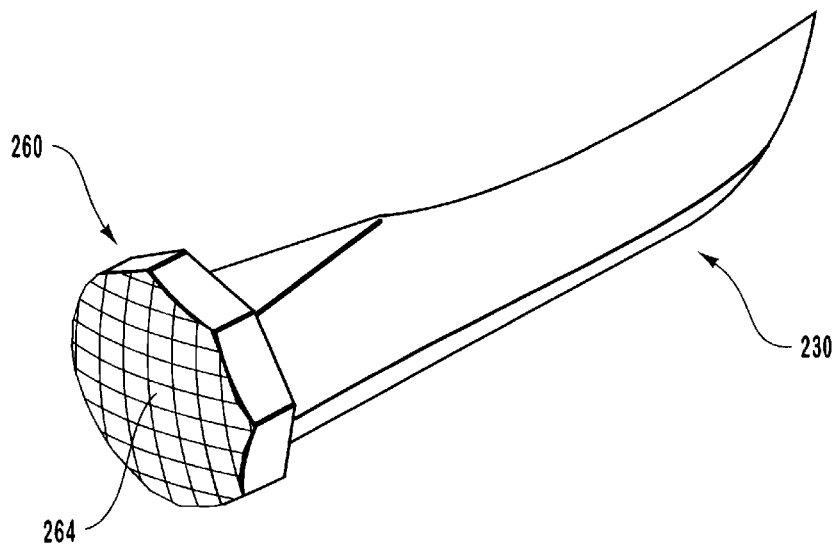
FIG. 17 is a perspective view of another embodiment of a dental wedge of the present invention which has no neck and a body which is integral with the head. The head has a textured proximal end.
Figure 18:
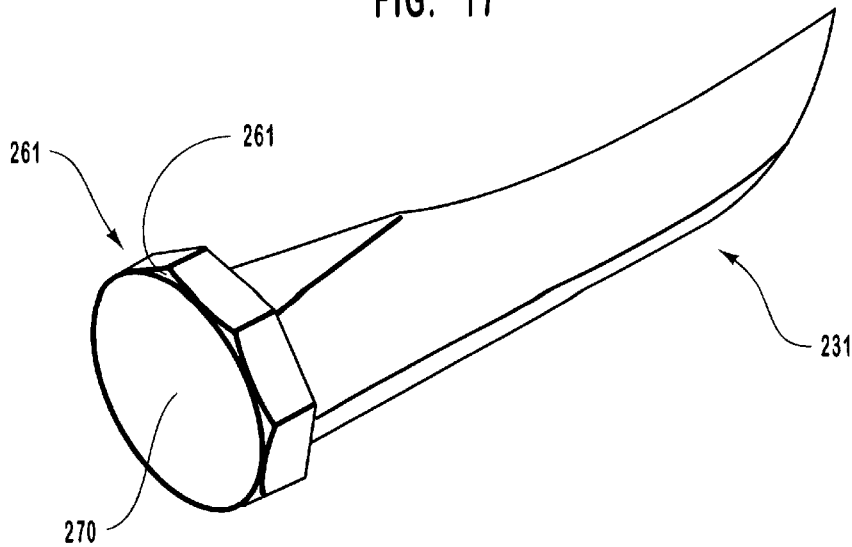
FIG. 18 is a perspective view of another embodiment of a dental wedge of the present invention which has no neck and a body which integral with the head. The head has a smooth proximal end.

As shown in FIG. 17 and FIG. 18, some embodiments of the present invention have a head directly coupled to the body without a neck. In such embodiments, the head is preferably larger than the body as are heads 260 and 261 of respective wedges 230 and 231 depicted in FIG. 17 and FIG. 18. Similarly, the heads of the wedges in the other embodiments may also be larger than their respective bodies. Wedge 230 is entirely integral as there is no cap. Proximal end 264 of head 260 is configured with a textured surface to minimize the potential for a dental instrument to slip while being urged against the instrument or as the instrument is pushed against the proximal end. Proximal end 265 of head 261 has a cap 270 which is formed from the same material as caps 70, 71 and 72. Cap 270 has an insertion prong (not shown) which fits into a chamber (not shown) in the body. Cap 270 may have any suitable configuration such as a convex shape as shown or a concave shape. Additionally, cap 270 may also be textured. Further, cap 270 and proximal end 264 may also be coated with a relatively tacky material to minimize slipping of dental instruments.

Since the body of the wedges is configured to be disposed within an interproximal space and to maintaining a matrix band in a desired orientation between adjacent teeth or otherwise maintaining a space between teeth, the body is preferably comprised of a rigid material, such as a relatively rigid plastic. The individual components of the wedges or the integral wedges can be formed by any means, such as thermoplastics or cast plastics formation techniques. One skilled in the art will appreciate that a variety of different methods are available for manufacturing the dental wedges. In the embodiments, wherein the wedge is entirely integral, the wedge may be molded from plastic into a rigid wedge. In the embodiments, wherein the wedge comprises two components, namely a cap configured to interlock within a chamber in the neck and head of a wedge and also an integral component. The integral component is a body, neck and at least a portion of the head. The cap is preferably separately formed into a resilient, compressible component which interlocks with a separately formed rigid component. The two components may be designed to interlock through the configuration of the insertion prong of the cap and the chamber. In yet another embodiment, the two components are molded to each other, such as by using a two-color mold to cause the components to chemically adhere to each other. Additionally, an adhesive may be placed between the two components such as thermal adhesive glue, an adhesive coating, an adhesive pad, and a pressure sensitive adhesive.

FIGS. 19–24 depict instruments which are particularly adapted for use with the inventive dental wedges. Each instrument is designed such that when the dental wedge is pushed into position or pulled out of an embrasure the wedge is securely grasped with an instrument with portions which are configured to be mated with the flat gripping surfaces of the head or neck.

Figure 19:
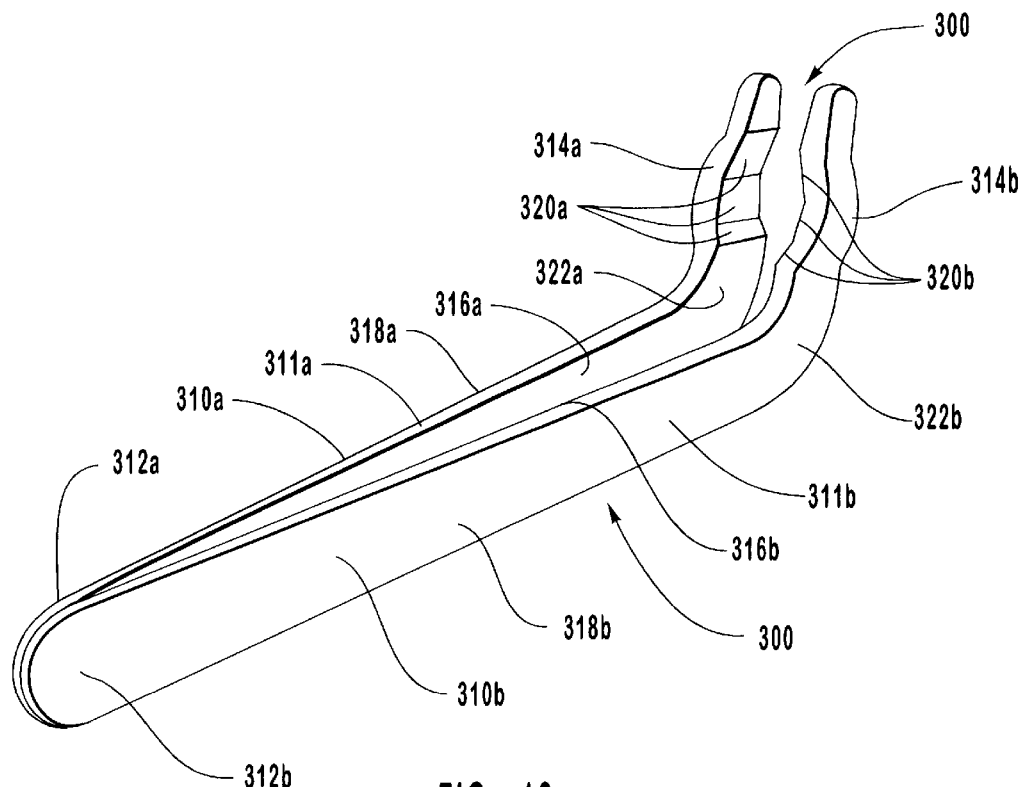
FIG. 19 is a perspective view of tweezers having prongs adapted for grasping a dental wedge by the neck or the head of the dental wedge.
Figure 20:
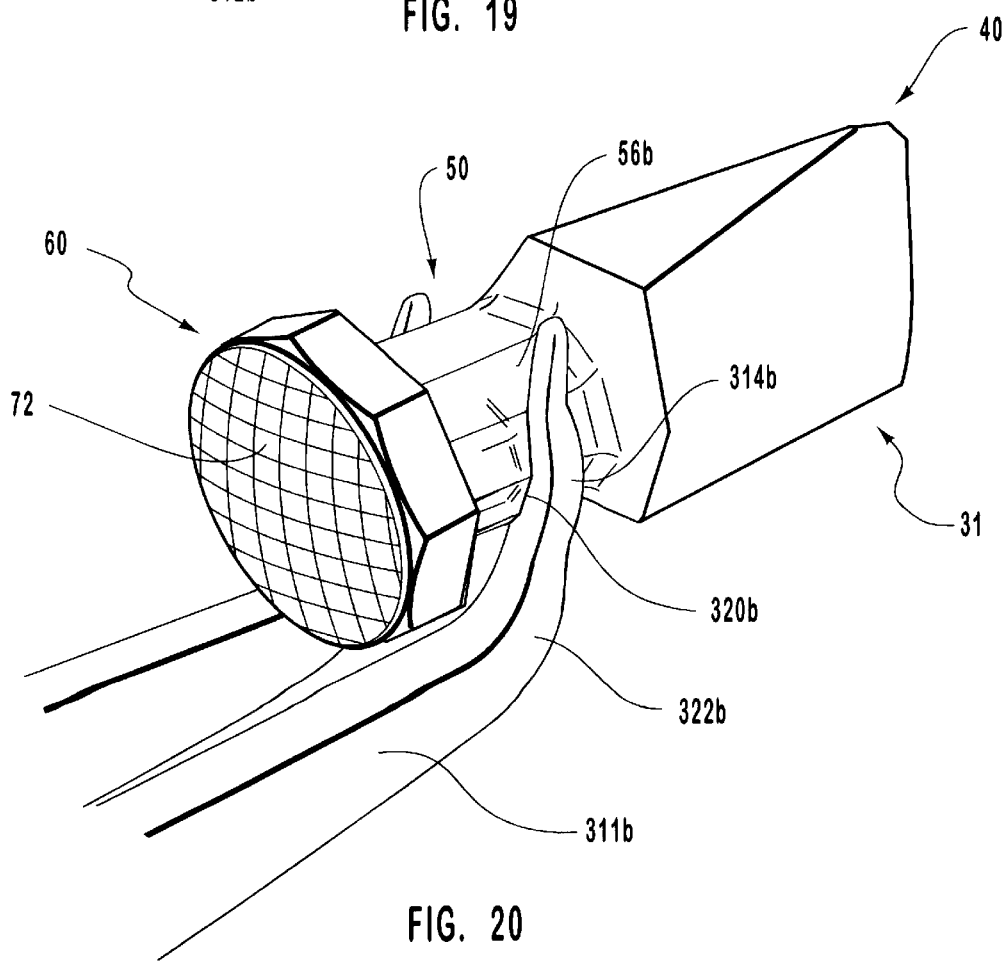
FIG. 20 is a perspective view of the prongs of the tweezers shown in FIG. 19 grasping a dental wedge by the neck of the dental wedge.

FIG. 19 and FIG. 20 depicts a pair of dental tweezers 300 adapted for grasping a dental wedge. The unique configuration of the tweezers enables a user to securely grasp a dental wedge which has a head or neck with a plurality of flat gripping surfaces. Tweezers 300 comprise a pair of elongated members 310*a–b*. Each elongated member has a handle portion 311*a–b* with a hinge end 312*a–b* opposite a grasping end 314*a–b*; and also an internal side 316*a–b* and an external side 318*a–b*. Internal side 316*a* is opposing internal side 316*b*. The internal side 316*a–b* of each elongated member 310*a–b* has a plurality of flat grasping surfaces 320*a–b* at each respective grasping end which are adapted to conform to more than two flat gripping surfaces of a head or neck of a dental wedge. The hinged ends 312a-b are joined together such that the flat grasping surfaces 320*a–b* of each respective grasping end can be moved together or apart by pivoting the elongated members 310*a–b*.

As shown in FIG. 19 and FIG. 20, each elongated member 310*a–b* is preferably curved at or near its respective grasping end 314*a–b* such that the tweezers have curved portions or prongs 322*a–b*. The curved prongs 322*a–b* or portion of the elongated members provide enhanced ability to introduce wedges into an remove wedge from all embrasures.

FIG. 20 depicts grasping ends 314*a–b* or prongs 322*a–b* grasping neck 50 of dental wedge 31. More specifically, flat grasping surfaces 320*a–b* are in a mated configuration with the flat gripping surfaces 56 of neck 50. Flat grasping surfaces 320*a–b* can also be mated with the flat gripping surfaces 66 of head 60. Although, any plurality of flat grasping surfaces may be located on the internal side of each elongated member, there are preferably at least three different flat surfaces which are integral and angled with respect to each other. More particularly, the plurality of flat grasping surfaces on the internal side of each elongated member are preferably configured for grasping a dental wedge with a head or neck having eight different gripping flat surfaces.

The combination of grasping ends 314*a–b*, more specifically prongs 322*a–b*, with flat grasping surfaces configured to be mated with the flat gripping surface of a head or neck of a wedge is an example of grasping means for simultaneously grasping more than two flat gripping surfaces of a head or neck of a dental wedge. The hinge end 312*a–b* and handle portion 311*a–b* of the elongated member 310*a–b* is an example of handle means for operatively moving the grasping means. Pliers such as pliers 90 shown in FIG. 11 can also be configured within the scope of the present invention with flat grasping surfaces in a similar configuration to the flat grasping surfaces of tweezers 300.

Figure 21:
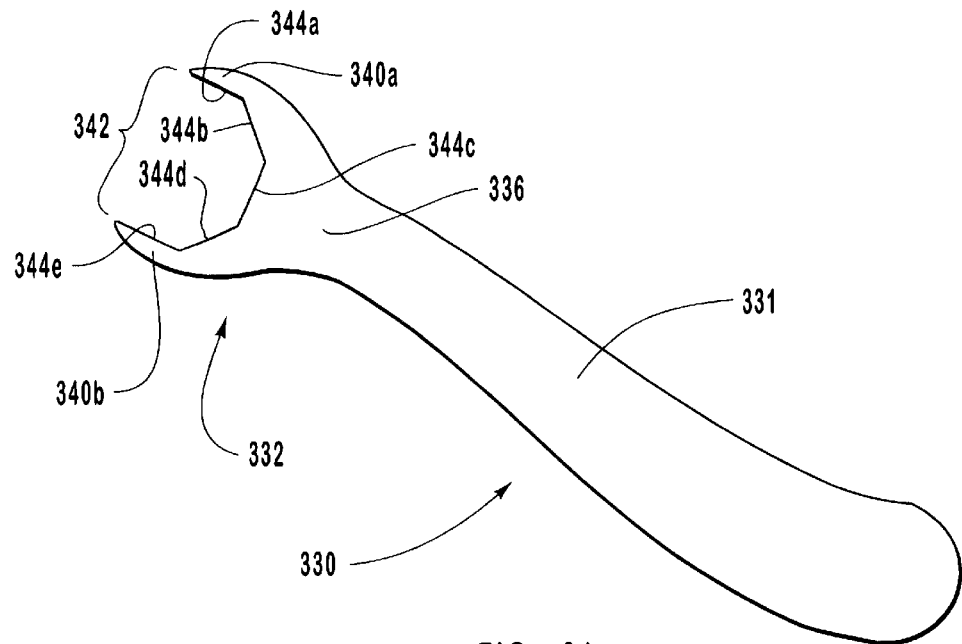
FIG. 21 is a perspective view of wrench having a grasping end adapted for grasping a dental wedge by the neck of the dental wedge.

FIG. 21 depicts a dental wrench 330 adapted for grasping a dental wedge. Wrench 330 comprises a handle 331 having an integral grasping open end 332. Open end 332 has two prongs 340*a–b* which define a grasping recess 342. Grasping recess 342 is depicted with five different grasping surfaces 344*a–e* which are adapted to conform to five different gripping surfaces of a head or neck of a dental wedge in a mated configuration. Such a dental wedge has a total of eight different gripping surfaces on either the head or the neck. Although, the wrench is depicted with five different gripping surfaces, the grasping recess may have at least three different flat grasping surfaces which may be coupled with at least three different flat gripping surfaces of the head or neck of wedge. Such a head or neck may be square or rectangular shaped.

Figure 22:
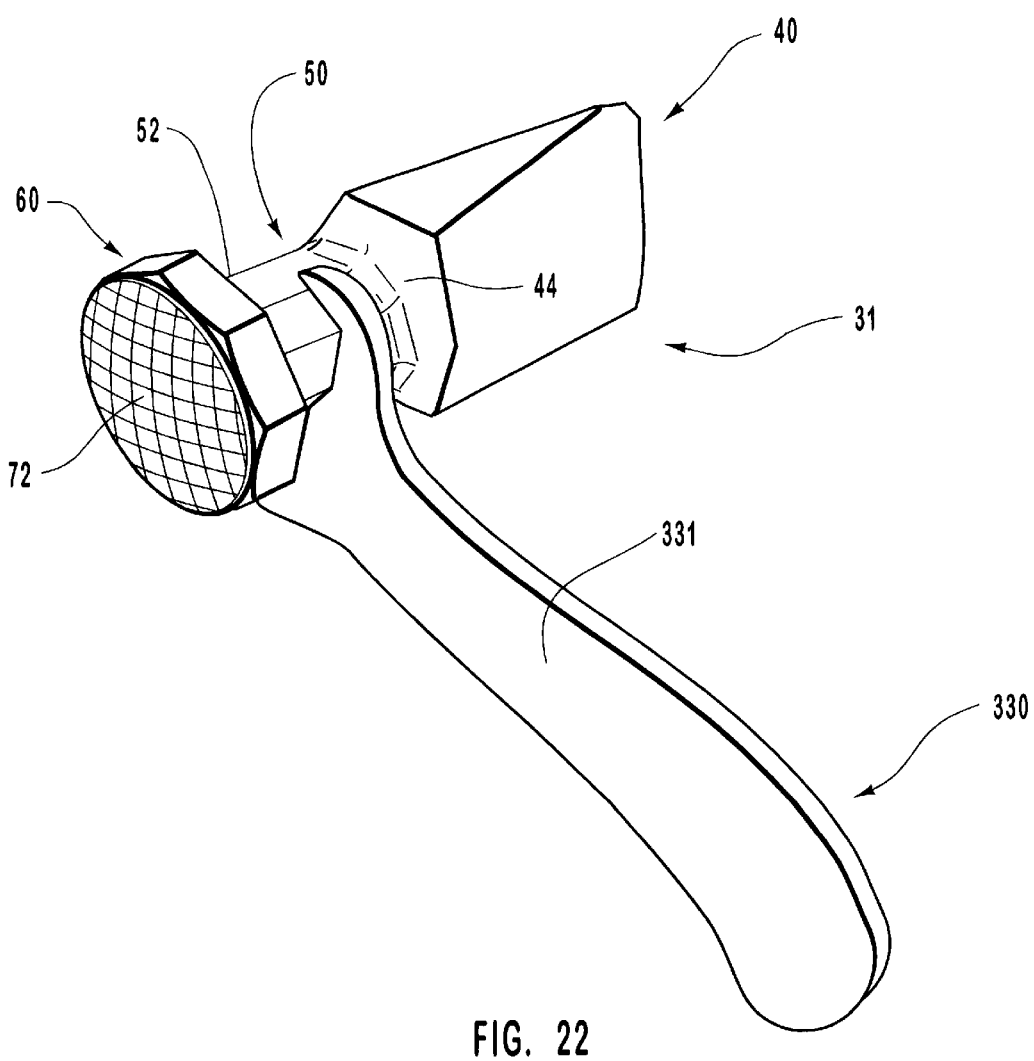
FIG. 22 is a perspective view of the wrench shown in FIG. 21 grasping a dental wedge by the neck of the dental wedge.

Although, wrench 330 enables a user to securely grasp a wedge with a head or neck having a plurality of flat gripping surfaces, wrench 330 is most suitable for grasping the neck of a wedge as shown in FIG. 22. After the grasping recess 342 contacts neck 50, wedge 31 may be pushed or pulled. Additionally, grasping recess may be slid or moved into an abutting position with either face 45 of body 40 or face 63 of head 60. Similarly, grasping ends 314*a–b* of tweezers 300 may also be slid or moved into an abutting position with either face 45 of body 40 or face 63 of head 60.

Wrench 330 is preferably integral and is also preferably formed from plastic. Additionally, handle 331 preferably has a neck 336 near open end 332 which is relatively flexible. The flexibility of neck 336 is useful as the wrench may then be bent to push a dental wedge into position or to pull a dental wedge out of an embrasure which may otherwise be difficult to reach.

Handle 331 is another example of handle means for operatively moving the grasping means. Grasping open end 332 or more specifically, grasping recess 342, is another example of grasping means for simultaneously grasping more than two flat gripping surfaces of a head or neck of a dental wedge.

Figure 23:
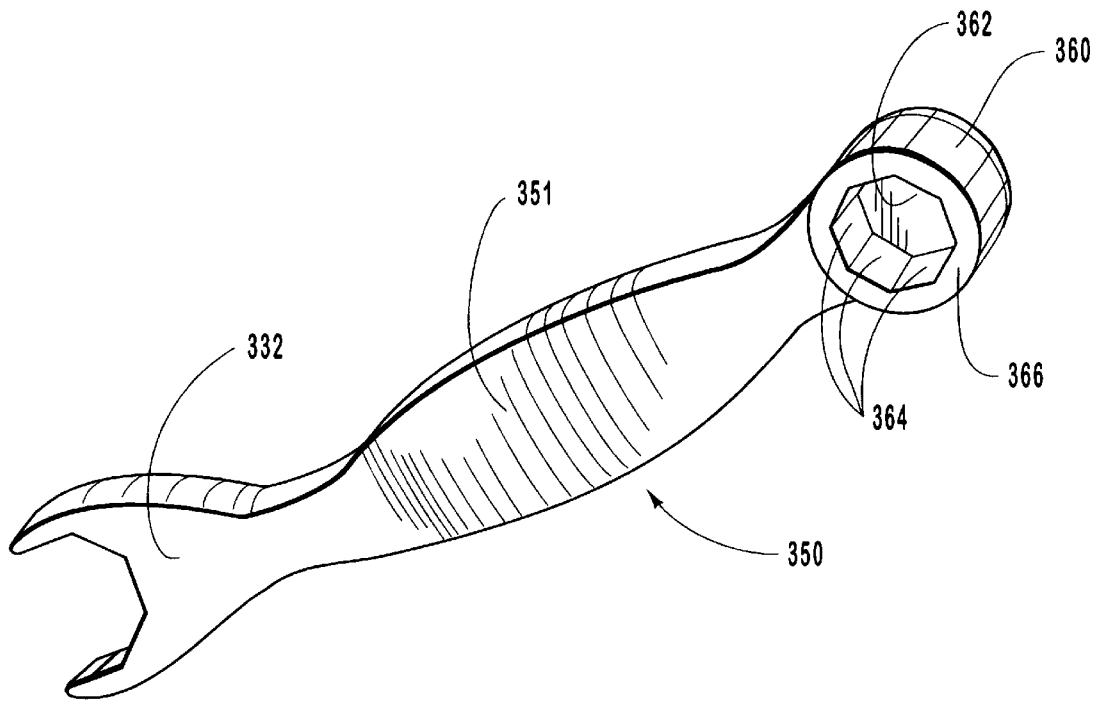
FIG. 23 is a perspective view of another embodiment of a wrench configured for use with dental wedges. The wrench has a grasping end adapted for grasping a dental wedge by the neck of the dental wedge and a socket end adapted for pushing on the head of a dental wedge.
Figure 24:
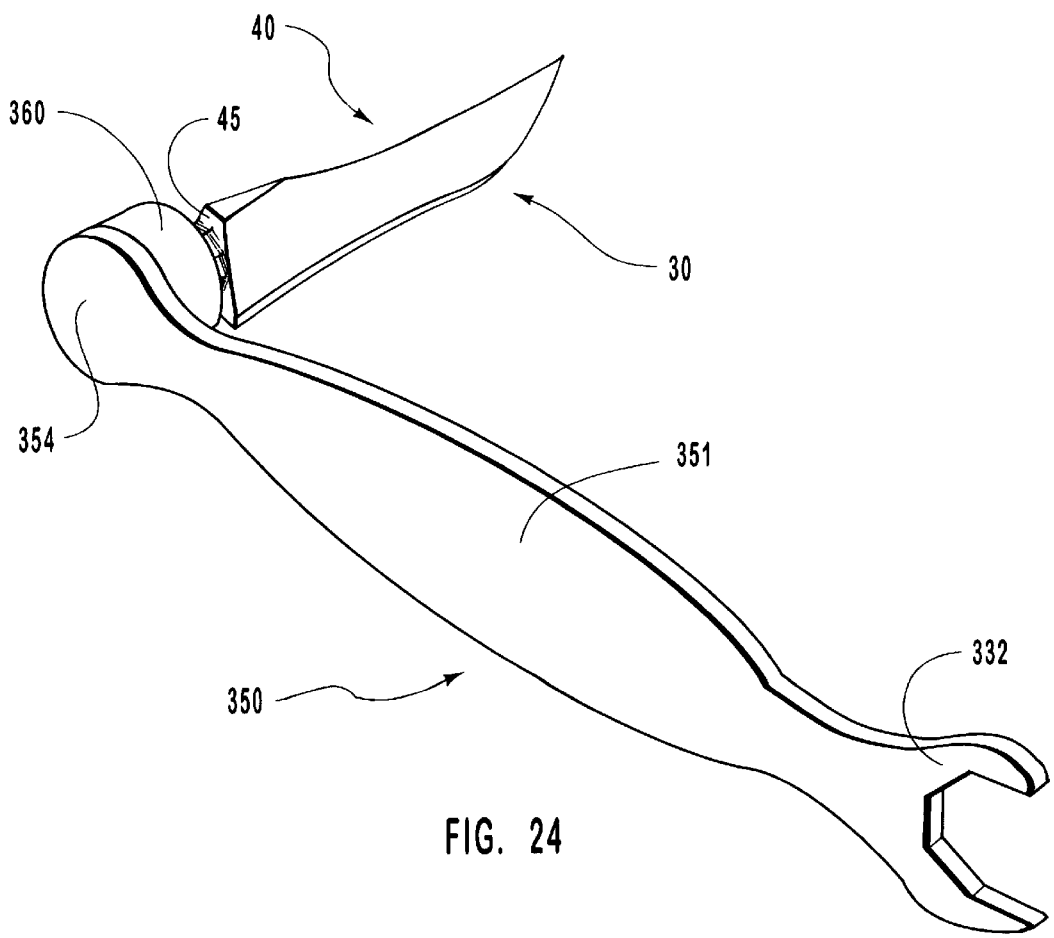
FIG. 24 is a perspective view of the socket end of the wrench shown in FIG. 23 pushing on the head of a dental wedge.

FIG. 23 and FIG. 24 depict a wrench 350 which comprises a handle 351 with an integral grasping open end 332 opposite an integral grasping socket end 354. A tube portion 360 extends from handle 351 at socket end 354. As seen in FIG. 23, tube portion 360 has a base 362 and a plurality of flat grasping surfaces 364 which are adapted to conform to a head of a dental wedge with flat gripping surfaces which correspond in number to the flat grasping surfaces of the tube portion.

FIG. 24 indicates that closed socket end 354, more particularly, the flat grasping surfaces 364 are sized and configured to be located around the head of wedge 30. Tube portion 360 preferably has a length which enables the base 362 to contact either the cap or the proximal end of the head of the wedge such that the base can be pushed against the cap or proximal end of the head of the wedge, as shown in FIG. 24. The rim 366 of the tube portion can also be used to push against face 45 of body 40. Whether base 362 or rim 366 is used to push a wedge into place or to twist a wedge, either configuration enables a dental wedge with a head having a plurality of flat gripping surfaces to be securely grasped and pushed.

Handle 351 is another example of handle means for operatively moving the grasping means. Grasping socket end 354 or more specifically, tube portion 360, is another example of grasping means for simultaneously grasping more than two flat gripping surfaces of a head or neck of a dental wedge.

In another embodiment, a wrench such as wrench 350 may be configured without a grasping open end such as open end 332. Accordingly, a dental wrench of the present invention may have only one grasping means or the wrench may have a first grasping means opposite a second grasping means which are connected by a handle.

Handle 351 is preferably primarily rigid near the socket end to better enable the instrument to be used to push a wedge. Wrench 350 is preferably entirely integral and is preferably formed from plastic.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed:

1. a dental wedge, comprising:
   (a) tapered body means for insertion within an interproximal space between two teeth, the tapered body means having a proximal end and a distal end;

(b) head means for moving the tapered body means with respect to an interproximal space between two teeth by a dental instrument, the head means having a proximal end and a distal end, the distal end of the head means being coupled to the proximal end of the tapered body means; and (c) a resilient, compressible cap attached to the proximal end of the head means.

2. A dental wedge as recited in claim 1, wherein the cap is formed from neoprene.

3. A dental wedge as recited in claim 1, wherein the cap has a textured surface.

4. A dental wedge as recited in claim 1, wherein the head means has a greater diameter than the tapered body means.

5. A dental wedge as recited in claim 1, wherein the head means has more than four different flat gripping surfaces extending about a circumference of the head means.

6. A dental wedge as recited in claim 1, wherein the head means has a transverse cross section in the shape of an octagon.

7. A dental wedge as recited in claim 1, wherein the distal end of the head means is coupled to the proximal end of the tapered body means by a neck.

8. A dental wedge as recited in claim 7, wherein the neck has a plurality of flat gripping surfaces extending about a circumference of the neck.

9. A dental wedge as recited in claim 7, wherein the neck is round.

10. A dental wedge as recited in claim 7, wherein the neck, the tapered body means, and a distal portion of the head means are integral.

11. A dental wedge, comprising:

(a) tapered body means for insertion within an interproximal space between two teeth, the tapered body means having a proximal end and a distal end;

(b) head means for moving the tapered body means with respect to an interproximal space between two teeth by a dental instrument, the head means having a proximal end and a distal end, the distal end of the head means being coupled to the proximal end of the tapered body means; the head means having more than four different flat gripping surfaces extending about a circumference of the head means; and (c) a resilient, compressible cap attached to the proximal end of the head means.

12. A dental wedge as in claim 11, wherein the distal end of the head means is coupled to the proximal end of the tapered body means by a neck means for receiving a grasping end of a dental instrument to move the tapered body means with respect to an interproximal space between two teeth, and for coupling the distal end of the head to the proximal end of the tapered body means.

13. A dental wedge as recited in claim 12, wherein the diameter of the neck means is smaller than the diameter of the proximal end of the tapered body means.

14. A dental wedge as recited in claim 12, wherein the diameter of the neck means is smaller than the diameter of the distal end of the head means.

15. A dental wedge as recited in claim 12, wherein the neck means has a plurality of flat surfaces extending about a circumference of the neck means.

16. A dental wedge as recited in claim 12, wherein the neck means has more than four different flat surfaces extending about the circumference of the neck means.

17. A dental wedge as recited in claim 12, wherein the neck means has a transverse cross section in the shape of an octagon.

18. A dental wedge as recited in claim 12, wherein the neck means has a plurality of flat surfaces extending about a circumference of the neck means, and wherein the flat surfaces of the neck means are offset with respect to the flat surfaces of the head means.

19. A dental wedge as recited in claim 12, wherein the neck means enables a grasping end of a dental instrument to push against the proximal end of the tapered body means, thereby pushing the wedge into a desired location; and to pull against the distal end of the head means to pull the wedge from a desired location.

* * * * *

UNITED STATES PATENT AND TRADEMARK OFFICE
CERTIFICATE OF CORRECTION

PATENT NO. : 5,890,900

DATED : April 6, 1999

INVENTOR(S) : Dan E. Fischer, Bruce S. McLean

Page 1 of 2

It is certified that error appears in the above-identified patent and that said Letters Patent are hereby corrected as shown below:

Col. 1, ln. 6: after "herein" change "are" to --is--

Col. 1, ln. 7: after "particularly, the" change "inventions" to --invention--

Col. 1, ln. 53: after "while the" delete [more]

Col. 2, ln. 16: after "within the" change "patients'" to --patient's--

Col. 3, ln. 28: after "may" and before "an" insert --be--

Col. 4, ln. 2: after "neck of" and before "wedge" insert --a--

Col. 4, ln. 13: after "to push" and before "the wedge" delete [the push]

Col. 5, ln. 20: after "which" and before "integral" insert --is--

Col. 5, ln. 28: after "view of" and before "wrench" insert --a--

Col. 5, ln. 56: after "off" and before "wedge" insert --the--

Col. 6, ln. 13: after "between the" change "patients'" to --patient's--

Col. 7, ln. 51: after "octagon," and before "decagon" delete [a]

Col. 10, ln. 64: after "FIG. 20" change "depicts" to --depict--

Col. 11, ln. 20: after "into" change "an" to --,or--

UNITED STATES PATENT AND TRADEMARK OFFICE
CERTIFICATE OF CORRECTION

PATENT NO. : 5,890,900

DATED : April 6, 1999

INVENTOR(S) : Dan E. Fischer, Bruce S. McLean

It is certified that error appears in the above-identified patent and that said Letters Patent are hereby corrected as shown below:

Col. 11, ln. 20: after "remove" change "wedge" to --wedges--

Col. 11, ln. 60: before "wedge" insert --the--

Col. 12, ln. 32: before "proximal" change "or" to --of--

Col. 12, ln. 63: after "claimed" insert --and desired to be secured by United States Patent is--

Signed and Sealed this

Twenty-second Day of August, 2000

Attest:

Q. TODD DICKINSON

*Attesting Officer*     *Director of Patents and Trademarks*